United States Patent
Chapman et al.

(10) Patent No.: US 8,268,991 B1
(45) Date of Patent: Sep. 18, 2012

(54) PROCESSES FOR PREPARING CERTAIN HEXAAZAISOWURTZITANES AND THEIR USE IN PREPARING HEXANITROHEXAAZAISOWURTZITANE

(75) Inventors: Robert D. Chapman, Ridgecrest, CA (US); Richard A. Hollins, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1268 days.

(21) Appl. No.: 12/022,930

(22) Filed: Jan. 30, 2008

Related U.S. Application Data

(63) Continuation-in-part of application No. 11/789,678, filed on Apr. 23, 2007, now Pat. No. 7,875,714.

(51) Int. Cl.
*C07D 487/00* (2006.01)
(52) U.S. Cl. .................. 540/475; 540/554; 540/556
(58) Field of Classification Search .................. 540/554, 540/475, 556
See application file for complete search history.

(56) References Cited

U.S. PATENT DOCUMENTS

| | | | |
|---|---|---|---|
| 5,693,794 A | 12/1997 | Nielsen | |
| 7,279,572 B2 * | 10/2007 | Cagnon et al. | 540/475 |
| 2004/0260086 A1 | 12/2004 | Cagnon et al. | |

OTHER PUBLICATIONS

Herve, Grégoire. Preparation and Structure of Novel Hexaazaisowurtzitane Cages. Chemistry—A European Journal. 12(12) 2006, 3339-3344.*

* cited by examiner

*Primary Examiner* — Rebecca Anderson
*Assistant Examiner* — Samantha Shterengarts
(74) *Attorney, Agent, or Firm* — Brian F. Drazich; Charlene A. Haley

(57) ABSTRACT

The present invention describes a novel heavy-metal-free sequence leading to a superior, more economical, and scalable process for the high efficiency conversion of hexaallyl-hexaazaisowurtzitane (HAllylIW) to hexa(1-propenyl) hexaazaisowurtzitane (HPIW) and hence via reaction with singlet oxygen and subsequent nitrolysis to hexanitro-hexaazaisowurtzitane (CL-20).

9 Claims, 10 Drawing Sheets

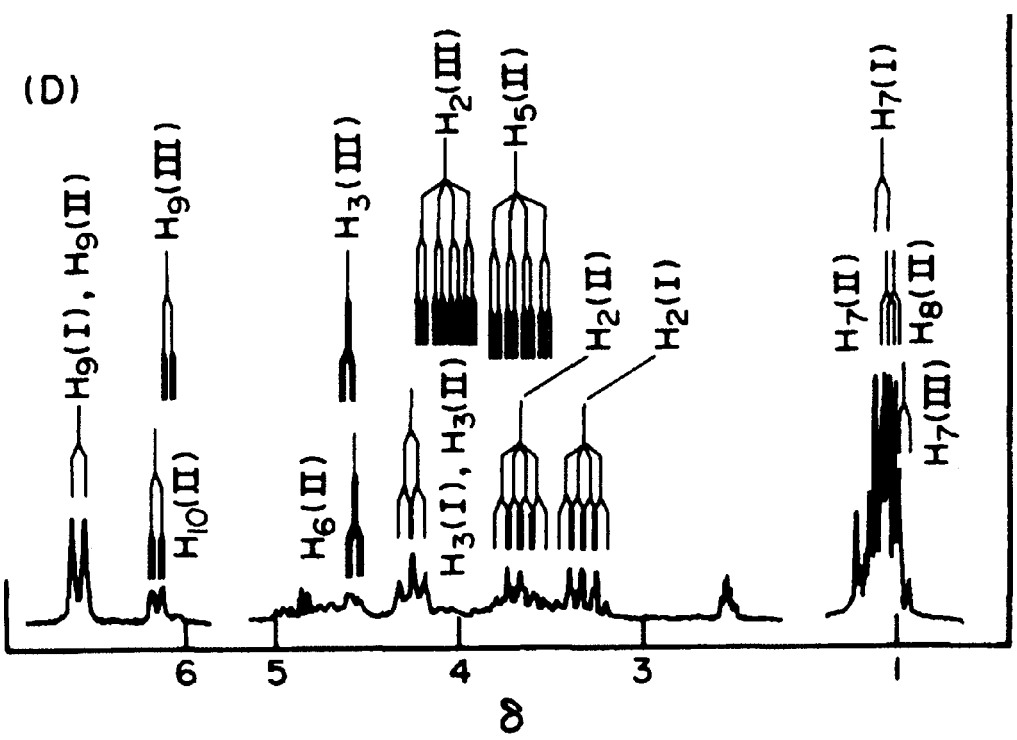
Figure 9 $^1$H NMR spectrum of lactaldehyde dimer (4)

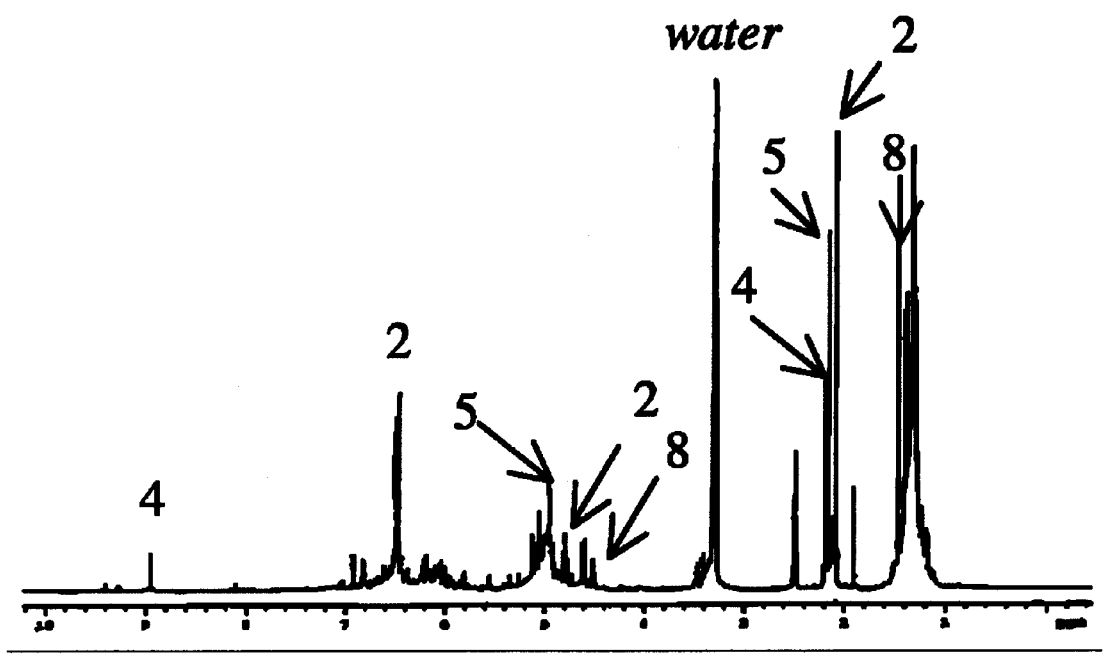
Figure 10 $^1$H NMR spectrum of methylgyoxal in DMSO-$d_6$ [12] (structure 8,[12] whose peaks are labeled, corresponds to methylglyoxal dimer 5 herein)

PROCESSES FOR PREPARING CERTAIN HEXAAZAISOWURTZITANES AND THEIR USE IN PREPARING HEXANITROHEXAAZAISOWURTZITANE

CROSS REFERENCE TO RELATED APPLICATIONS

This application claims priority under 35 U.S.C. §120 and is a continuation-in-part of U.S. patent application Ser. No. 11/789,678 filed Apr. 23, 2007, now U.S. Pat. No. 7,875,714.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

One of the most important new energetic compositions for ordnance applications is hexanitrohexaazaisowurtzitane (CL-20), but its production process suffers from several economic and environmental disadvantages, mostly related to requirements for benzylamine starting material and for heavy metal (typically, palladium) catalysts. It is desirable to prepare the hexaazaisowurtzitane cage in a form that is directly nitrolyzable to CL-20 without a requirement for expensive benzylamine starting material or heavy metal catalysts. The present invention relates to processes for preparing certain hexaazaisowurtzitanes and their use in preparing hexanitrohexaazaisowurtzitane that does not require benzylamine starting material or heavy metal catalysts, thus introducing a new, lower-cost, less wasteful, and environmentally cleaner process to produce CL-20.

BACKGROUND OF THE INVENTION

The recent publication by French researchers (Cagnon, G.; Eck, G.; Hervé, G.; Jacob, G. U.S. Pat. No. 7,279,572 (2007); Hervé, G.; Jacob, G.; Gallo, R. *Chem. Eur. J.* 2006, 12, 3339) that the synthesis scheme originally proposed by Nielsen (Nielsen, A. T.; Nissan, R. A.; Vanderah, D. J.; Coon, C. L.; Gilardi, R. D.; George, C. F.; Flippen-Anderson, J. *J. Org. Chem.* 1990, 55, 1459) yields hexaallylhexaazaisowurtzitane (HAllylIW) provided us the opportunity to explore the potential of HAllylIW for use in new routes for the synthesis of hexanitrohexaazaisowurtzitane (CL-20). With respect to the synthesis of HAllylIW, however, it is important to note that we have confirmed that the scheme devised by Nielsen of condensation of certain primary amines with glyoxal to produce hexaazaisowurtzitane derivatives readily forms HAllylIW in solution when allylamine is condensed with glyoxal. However, under the conditions prescribed by Nielsen, no precipitate of HAllylIW is formed. We believe that the absence of such a product precipitate may have contributed to Nielsen's inability to isolate HAllylIW from the reaction of allylamine with glyoxal. This failure of HAllylIW to precipitate may have been the predominant factor contributing to Nielsen's erroneous conclusion that his efforts to extend the isowurtzitane synthesis to amines of this type were unsuccessful, notwithstanding that allylamines were expected to produce hexaazaisowurtzitanes.

BRIEF DESCRIPTION OF THE DRAWINGS

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments, which are illustrated schematically in the accompanying drawings and in the appended claims.

FIG. 9 is a chart of the $^1$H NMR spectrum of lactaldehyde dimer (4).

FIG. 10 is a chart of the $^1$H NMR spectrum of methylglyoxal in DMSO-$d_6$.

SUMMARY OF THE INVENTION

Figure 1:
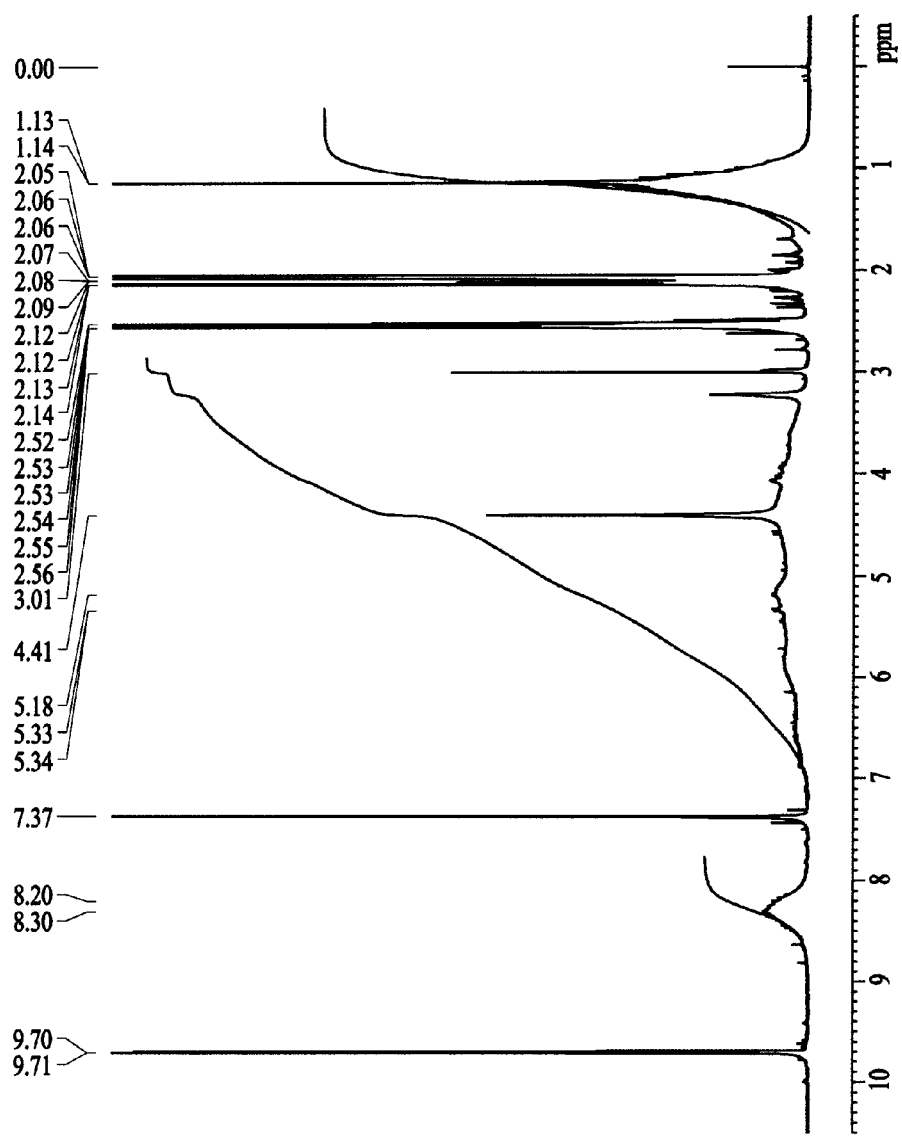
FIG. 1 is a chart of the $^1$H NMR absorption spectra of a mixture of oxidation products of HPIW.

The present invention demonstrates new routes to CL-20 that meet the desired criteria of avoiding benzylamine starting material and heavy metal catalysts. It employs less expensive allylamine starting material and uses an alkali-metal strong-base catalyst.

Heretofore, all synthetic routes used to prepare the hexaazaisowurtzitane cage for production of CL-20 have depended on the condensation of benzylamine with glyoxal, originally developed by Nielsen, as noted above. CL-20 has remained nearly prohibitively expensive, however (as a potential large-scale replacement for the explosive ingredient octahydro-1,3,5,7-tetranitro-1,3,5,7-tetrazocine (HMX), for example), due mainly to the high cost of benzylamine starting material and of hydrogenolysis steps involving palladium catalyst used in the debenzylation of hexabenzylhexaazaisowurtzitane (HBIW) intermediate in the course of preparing acylhexaazaisowurtzitane intermediates, such as tetraacetyldiformylhexaazaisowurtzitane (TADF), tetraacetylhexaazaisowurtzitane (TADA or TADH or TAIW), or hexaacetylhexaazaisowurtzitane (HAIW).

The by-product of hydrogenolytic debenzylation of HBIW, toluene, is not economically or cleanly reconverted to benzylamine (only via chlorination followed by amination), so benzyl is not a clean, recoverable protecting group in that system. Various researchers ((a) "Lower Cost, Improved Quality CL-20 Energetic Material"; https://www.dodmantech.com/successes/Navy/weapons/weapons_Lower-CostCL20_120805.pdf; (b) Wardle, R. B.; Hinshaw, J. C. U.S. Pat. No. 6,147,209 (2000); (c) Wardle, R. B.; Hinshaw, J. C. U.S. Pat. No. 7,129,348 (2006); and references therein) have addressed process development for reducing the cost of CL-20 production, but have not approached cost reduction by developing a fundamentally different synthetic route to the hexaazaisowurtzitane cage such as is disclosed by the present invention.

In the work disclosed here, we have applied the chemical transformation of base-catalyzed isomerization of allylamines into 1-propenylamines to known hexaallylhexaazaisowurtzitane (HAllylIW) (using potassium tert-butoxide base) to prepare a new derivative, hexa(1-propenyl)-hexaazaisowurtzitane (HPIW). (This new derivative should not be confused with hexapiperonyl-hexaazaisowurtzitane, also designated HPIW by Tsai, H.-J. et al. Hua Hsuch [*Chemistry*] (*Taipei*) 2003, 61, 199.) We employed photooxygenation of HPIW by singlet oxygen—using oxygen gas photolyzed by a quartz halogen lamp in the presence of a tetraphenylporphine sensitizer—in order to oxidize some of the 1-propenyl substituents to formyl substituents. Although the oxidation reaction did not go to completion to produce hexaformylhexaazaisowurtzitane, the partially oxidized product—a polyformylhexaazaisowurtzitane—underwent nitrolysis to form CL-20 in a clean reaction. The nitrolysis of this intermediate is more efficient than direct nitrolysis of HAllylIW. Furthermore, we demonstrate that the new intermediate HPIW undergoes direct nitrolysis to form CL-20. This reactivity of the enamine HPIW is explainable as a mechanistically reasonable transformation. The reaction mechanism for photooxygenation of HPIW (Scheme 2), below, was elucidated in the course of quantifying the steps of the new sequences (Scheme 1), below. Those results are disclosed and discussed here.

DETAILED DESCRIPTION OF THE INVENTION

All synthetic routes used to prepare the hexaazaisowurtzitane cage for production of CL-20 depend on the condensation of benzylamine with glyoxal, originally developed by Nielsen, as referenced above. As noted above, CL-20 has remained nearly prohibitively expensive mainly due to the high cost of benzylamine starting material and of hydrogenolysis steps involving palladium catalyst used in the debenzylation of hexabenzylhexaazaisowurtzitane (HBIW) intermediate in the course of preparing acylhexaazaisowurtzitane intermediates.

An alternative benzylamine-free route to a hexaacyl-hexaazaisowurtzitane precursor to CL-20 was envisioned following the recent report by Hervé et al. (SNPE France) of a preparation of hexaallylhexaazaisowurtzitane (HAllylIW) from allylamine and glyoxal ((a) Cagnon, G.; Eck, G.; Hervé, G.; Jacob, G. U.S. Pat. No. 7,279,572 (2007); (b) Hervé, G.; Jacob, G.; Gallo, R. *Chem. Eur. J.* 2006, 12, 3339). The new route we envisioned was to utilize HAllylIW in a well-known isomerization reaction of allylamines into 1-propenylamines. The resulting hexa(1-propenyl)-hexaazaisowurtzitane could then be oxidized by singlet oxygen (which may be generated by dye-sensitized photolysis of oxygen gas, for example) via another well-known transformation: cleavage of the C=C bond of propenylamines to produce formamides (Foote, C. S.; Lin, J. W.-P. *Tetrahedron Lett.* 1968, 3267). The resulting hexaformylhexaazaisowurtzitane is another example of the class of hexaacylhexaazaisowurtzitanes that may be susceptible to direct nitrolysis to CL-20.

Following several failed attempts to reproduce the allylamine-glyoxal reaction according to conditions reported by Hervé et al., we were—through some process development—able to successfully recover HAllylIW by significantly modifying the isolation conditions reported by Hervé et al. (cf. Experimental Section). Newer preparations of hexaallyl-hexaazaisowurtzitane (HAllylIW) under conditions discussed herein have recently given isolated, purified yields of HAllylIW around 26%, closer to the 20-25% previously reported by Hervé et al. and somewhat lower than the crude yield of 33% which we initially calculated. Thus, HAllylIW has been prepared by us in 26% to 33% yield, somewhat better than the 20-25% reported by Hervé et al.

The required rearrangement of HAllylIW was achieved (Equation 1) by base-catalyzed isomerization (Price, C. C.; Snyder, W. H. *Tetrahedron Lett.* 1962, 69). Clean, efficient isomerization of HAllylIW to hexa(1-propenyl)hexaazaisowurtzitane (HPIW) was effected—essentially quantitatively—by potassium t-butoxide (t-BuOK) base in dimethyl sulfoxide (DMSO) at room temperature in about 6 hours (also at 80° C. in about ¼ hour). We also demonstrated that the isomerization was efficiently achieved by introducing potassium t-butoxide as its conveniently available tetrahydrofuran solution into a solution of HAllylIW in DMSO or in dimethylformamide (DMF). Reactions in such about 1:1 solvent mixtures typically proceeded to completion in an overnight run. However, tetrahydrofuran (THF) as the sole solvent did not allow isomerization at room temperature, even on prolonged reaction. As in previous similar transformations of this type ((a) Sauer, J.; Prahl, H. *Tetrahedron Lett.* 1966, 2863; (b) Carlsen, P. H. J.; Jørgensen, K. B. *J. Heterocycl. Chem.* 1997, 34, 797), the allylamine-to-propenylamine isomerizations require only catalytic t-butoxide; some of our successful runs employed ⅓ equivalent of potassium t-butoxide per allyl substituent.

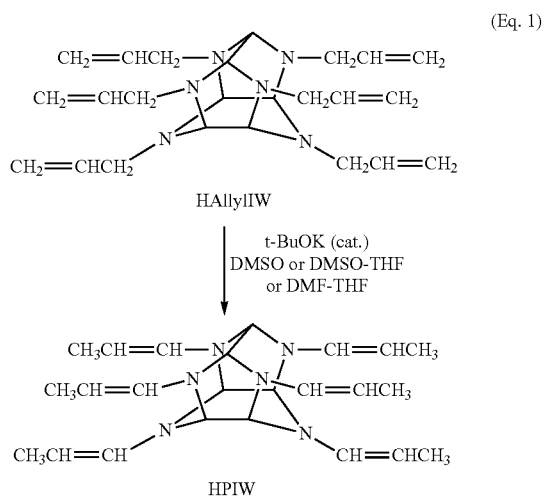

(Eq. 1)

HPIW was most easily purified (sufficiently for subsequent reactions) by removing solvent(s) under high vacuum and redissolving the HPIW in a suitable solvent in which residual potassium t-butoxide is insoluble. We initially chose benzene-$d_6$ for the sake of characterizing the dissolved HPIW and subsequent reaction products by NMR. Potassium t-butoxide has sufficiently low solubility in benzene that this is an effective purification method. However, other hydrocarbon solvents in which potassium t-butoxide has low solubility, such as toluene or xylene or even some aliphatics, are suitable for this process.

From analyses of four solutions of t-butanol-potassium t-butoxide mixtures in DMSO-$d_6$—quantified by integration of the quaternary carbon absorptions vs. those of DMSO-$d_6$ (i.e., all non-protiated carbons)—linear regression of a plot of mole fraction of t-butoxide vs. quaternary carbon chemical shift produced the following relationship, useful for determining potassium t-butoxide content in DMSO-$d_6$ solutions by $^{13}$C NMR:

$$X_{t\text{-}BuO^-} = 49.17 - \delta_{13_C}{}^{quat}/1.36$$

This regression estimates a chemical shift of δ 66.87 for pure t-butanol in DMSO-$d_6$, comparing very favorably with a literature value of δ 66.88.

The $^1$H and $^{13}$C NMR spectra of HPIW in various solvents indicate that it exists in a few (two to four) rotational isomers (rotamers) due to cis-trans isomerism of the propenyl substituents and restricted rotation about the N-propenyl bonds. Other examples of exo-heterocyclic enamines, N,N-dimethylaminomethylene-substituted pyrazoles, exhibit complex NMR spectra due to rotamers, as well (Kölle, U.; Kolb, B.; Mannschreck, A. *Chem. Ber.* 1980, 113, 2545).

HPIW was next subjected to oxidation by singlet oxygen (as is discussed in detail below), generated by halogen-lamp photolysis of oxygen gas, sensitized by catalytic amounts of zinc tetraphenylporphine (Equation 2). The transformation of enamines to formamides via photooxygenation has been reported to occur in a variety of different solvents (Foote, C. S.; Dzakpasu, A. A. *Tetrahedron Lett.* 1975, 1247.).

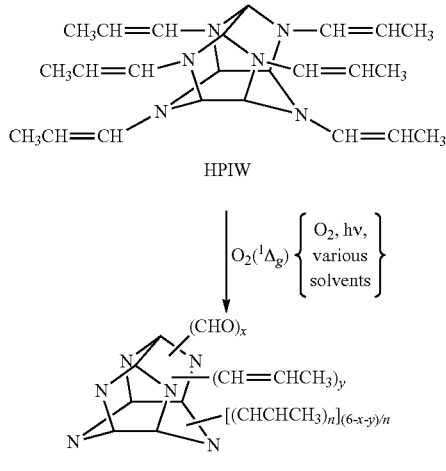

(Eq. 2)

The crude oxidation product (structure 6 in Equations 2 and 3) is a hexaazaisowurtzitane cage with indeterminate numbers of formyl, 1-propenyl, and saturated polymer chain substituents and where n is indeterminate (0≦n), 0≦x≦6, 0≦y≦6, and 0≦x+y≦6. Integration of the various broad absorptions of the $^1$H NMR spectra (FIG. 1) suggested that the average extent of oxidation of 1-propenyl substituents to formyl was typically between three and four substituents per hexaazaisowurtzitane cage (i.e., x=about 3 or 4) before significant precipitation may have prevented further oxidation.

Table 1 lists the variety of conditions that were attempted to effect photooxygenation of HPIW to polyformylhexaazaisowurtzitane derivatives.

TABLE 1

Conditions of photooxygenation of HPIW

| Solvent system | Temperature | Reaction time |
|---|---|---|
| $C_6D_6$ | R.T. | 3 h |
| 2:1 $C_6D_6$-acetone-$d_6$ | 0° C. | 8 h |
| 3:5 $CDCl_3$-$CD_2Cl_2$ | 0° C. | 3 h |
| 1:1 $C_6H_6$-DMSO-$d_6$ | 0° C. | 3 h |
| acetone-$d_6$ | dry ice-EtOH bath | 6 h |
| 1:5 $CD_2Cl_2$-$CDCl_3$ | dry ice-EtOH bath | 0.8 h |

The products of some photooxygenation reactions were subjected to nitrolysis after isolation from reaction suspensions by removal of all volatiles (solvent and acetaldehyde by-product). An initial run utilizing a mixture of about 98% nitric acid and acetonitrile-$d_3$ produced a minor amount of CL-20 (<10%)—confirmed by HPLC analysis as well as $^1$H and $^{13}$C NMR spectrometry—in a complex mixture after 6 days of reaction at ambient temperature. (Such prolonged reaction conditions significantly hydrolyzed acetonitrile ultimately to acetic acid.) In another run, the very viscous oily residue from a photooxygenation reaction was subjected to nitrolysis conditions using about 98% nitric acid in the presence of Nafion NR50 beads as a strong Brønsted acid catalyst (Equation 3). Nafion® resins are perfluorinated ion-exchange materials composed of carbon-fluorine backbone chains and perfluoro side chains containing sulfonic acid groups. Nafion NR50 is a polymer of the general structure:

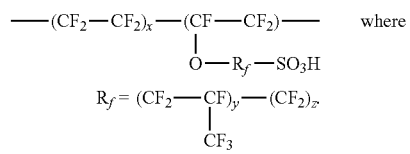

The application of Nafion® resins as versatile heterogeneous catalysts in organic transformations has been well established (Aldrich Technical Bulletin AL-163 and references therein). Other known strong Brønsted acid catalysts may be screened for efficiency in promoting this conversion, and those being efficacious will be suitable replacements for Nafion NR50.

(Eq. 3)

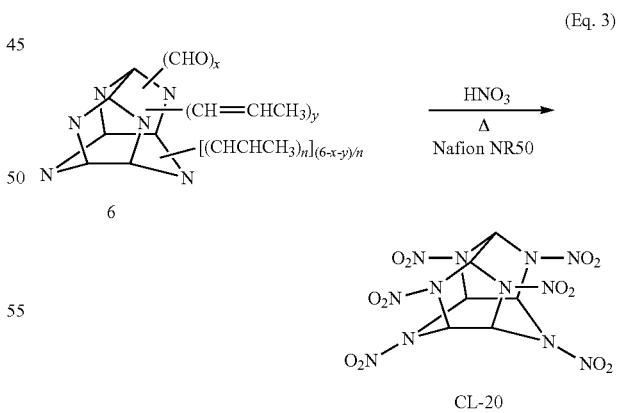

Figure 2:
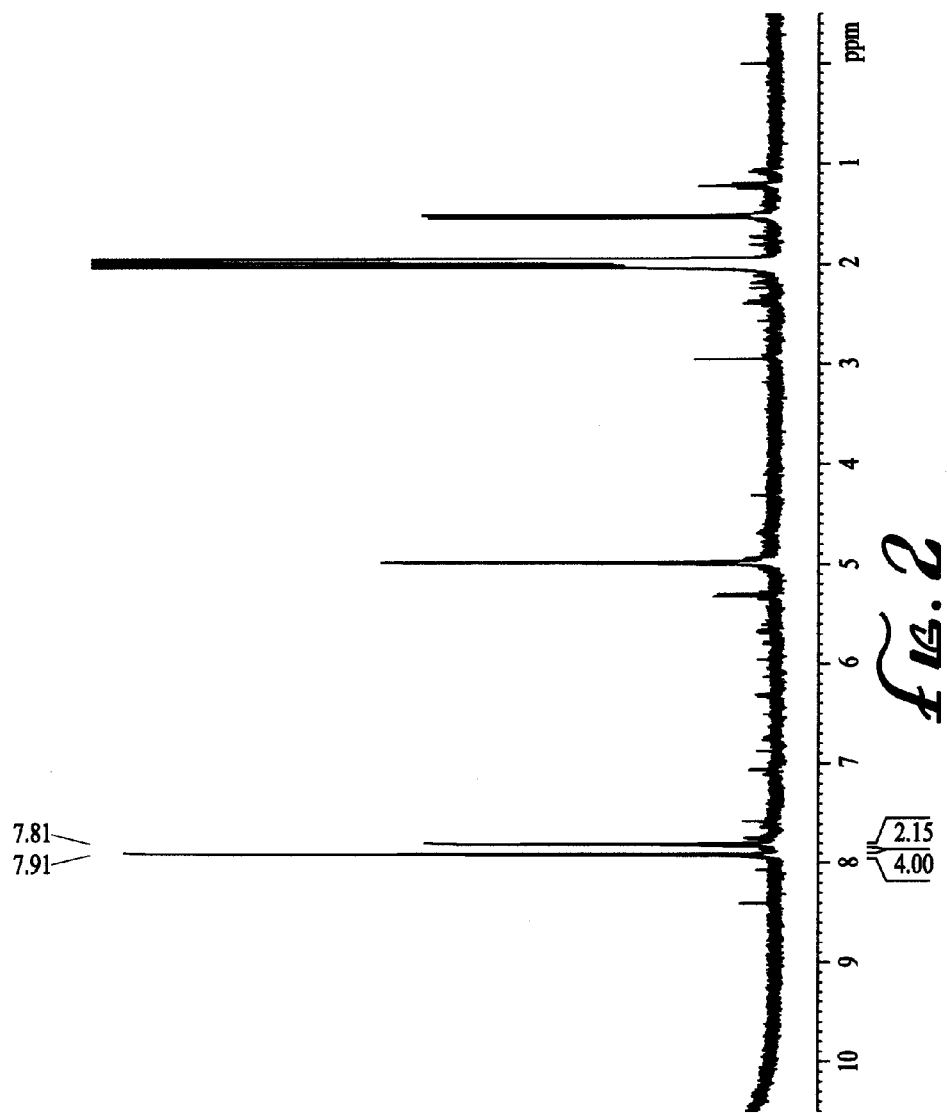
FIG. 2 is a chart of the $^1$H NMR absorption spectra of hexaazaisowurtzitane.

Reflux of the reaction solution for a total of about 30½ hours resulted in a surprisingly clean conversion of the crude polyformyl intermediate to CL-20. CL-20 is the predominant constituent in the spectral region attributable to hexaazaisowurtzitane species as shown by FIG. 2.

In parallel with the success of the nitrolysis of a crude product (structure 6 in Equations 2 and 3) of photooxygenation of HPIW, an experiment to directly nitrolyze HPIW itself was carried out. Out of concern for possible hydrolysis of enamine HPIW—which could lead to disruption of the cage and degradation of intermediates—from the minor water content of the about 98% nitric acid, fuming sulfuric acid was added to nitric acid to ensure anhydrous conditions for nitrolysis. An aliquot of the reaction mixture after 4 hours' reflux, added to dichloromethane-$d_2$ for NMR analysis, showed significant CL-20 content. The mixture was not quite as clean as the nitrolysis of the photooxygenation product of HPIW, but neither had the nitrolysis reaction proceeded as long.

We have discovered that displacement of substituents on the hexaazaisowurtzitane cage is superior to nitrolysis of α-unsubstituted alkyl derivatives (such as would be formed by initial nitration of allyl substituents in HAllylIW). For example, in the reports of Hervé et al. of new hexaazaisowurtzitanes, treatment of 1 g of HAllylIW with mixed acid produced a yellow solid (whereas CL-20 is colorless or white) that contained a detectable amount of CL-20, but no yield was specified. In contrast, the isomerization disclosed here on HAllylIW produces more easily removed substituents—following their initial nitration in HPIW—and the content of CL-20 in the nitrolysis mixture is high.

A careful review of literature on oxidations of enamines by singlet oxygen (Martin, N. H.; Jefford, C. W. *Helv. Chim. Acta* 1982, 65, 762); (Cook, A. G. in: Cook, A. G. *Enamines: Synthesis, Structure, and Reactions,* 2nd Edition; Marcel Dekker, 1988; Chapter 5.) suggested that the typical mechanism of oxidation followed in this transformation could proceed via a specific unusual regiochemical course in the case of conformationally restricted enamines presented by the structure of hexa(1-propenyl)hexaazaisowurtzitane (HPIW). Specifically, the 1-propenyl substituents at $N_2$ and $N_{12}$ (according to isowurtzitane nomenclature for hexaazaisowurtzitanes) (Crampton, M. R.; Hamid, J.; Millar, R.; Ferguson, G. *J. Chem. Soc. Perkin Trans.* 2 1993, 923); (Bellamy, A. J. *International Annual Conference of ICT [Proc.]* 2000, 31st (Energetic Materials), 109/1.) could be proximately oriented such that peroxide-substituted ionic intermediates (structure 1 in Scheme 2, below) formed from addition of singlet oxygen to the propenyl double bonds (following formation of a transient charge-transfer complex) (Martin, N. H.; Jefford, C. W. *Tetrahedron Lett.* 1981, 22, 3949.) could reasonably link the $N_2$ and $N_{12}$ substituents intermolecularly (i.e., between the two substituents within one hexaazaisowurtzitane molecule) via path b rather than intramolecularly—which typically leads to 1,2-dioxetane intermediates that rapidly cleave to an amide product plus a cleaved carbonyl product—via path a. Both pathways are feasible for hexaazaisowurtzitane structures.

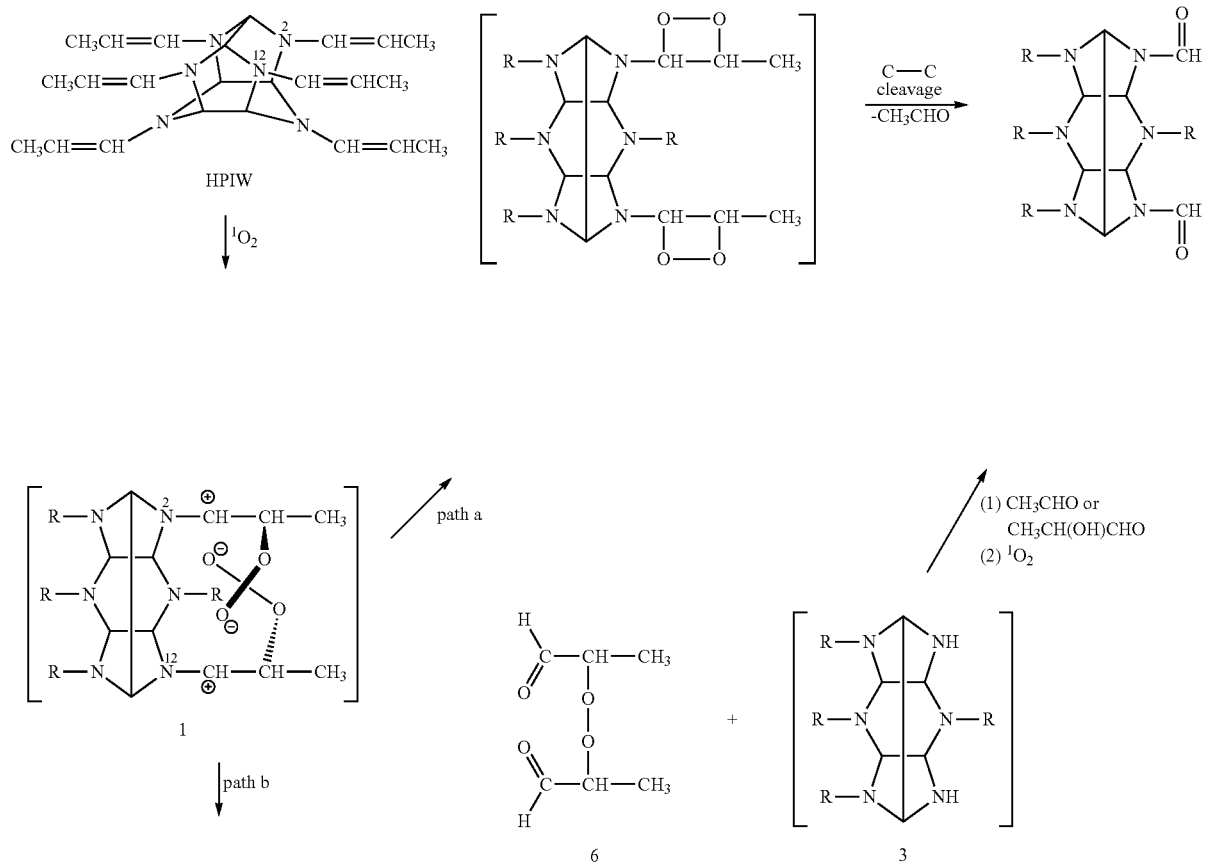

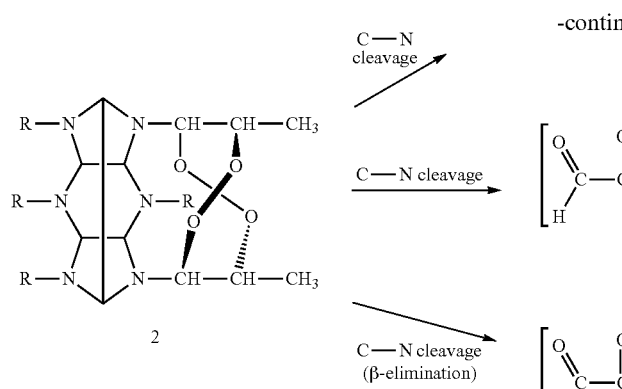
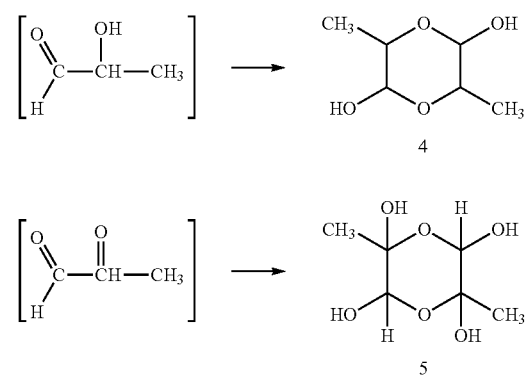

R = H or peroxide intermediate or CHO

Path a leads initially to 1,2-dioxetane intermediates and ultimately to the originally desired N-formyl derivatives of hexaazaisowurtzitane. However, path b appears to be able to form 1,2,5,6-tetroxocane derivatives (structure 2), which may be expected to be much more stable than alternative 1,2-dioxetane intermediates. Several other 1,2,5,6-tetroxocane derivatives have been isolated (Baranova, N. M.; Yakusheva, A. D.; Komarov, P. N. J. Org. Chem. USSR 1978 14, 2210); (Kim, H.-S.; Begum, K.; Ogura, N.; Wataya, Y.; Nonami, Y.; Ito, T.; Masuyama, A.; Nojima, M.; McCullough, K. J. J. Med. Chem. 2003, 46, 1957.) and may have quite high stabilities. (For example, one member of this class, 5,8α,13,16α-tetramethyldinaphtho[2,1-c,2',1'-g][1,2,5,6]tetroxocane, has a melting point of 230° C.) (Jefford, C. W.; Rossier, J.-C.; Kohmoto, S.; Boukouvalas, J. Helv. Chem. Acta. 1985, 68, 1804.) The saturated nature of the bonding in tetroxocane intermediates such as structure 2 is more consistent with $_1$H NMR chemical shifts which were actually observed for the photooxygenation product than the bonding in previously speculated polyformylpoly(1-propenyl)hexaazaisowurtzitane species would be: δ~1.14 vs. δ~1.60 seen in the HPIW reactant.

Peroxide (tetroxocane) intermediates such as structure 2, being hemiaminals (α-oxygen-substituted alkylamines), would also be expected to be fairly readily nitrolyzable—more so than would be saturated polymeric substituents that might be consistent with the $_1$H NMR chemical shifts. Finally, proof of the hypothesized peroxide-intermediate mechanism was obtained from new samples of the products of photooxygenation reactions. A solid sample of product prepared in a new run in acetone solvent, when redissolved in dimethyl sulfoxide, produced a dramatic positive peroxide test result with acidified starch-iodide solution. A sample of crude reaction solution in 1:1 DMSO-acetone from a second new run similarly gave a positive qualitative peroxide test result. A quantitative titration for peroxide content in the latter reaction solution suggests that peroxide intermediates, such as structure 2, have finite stability, as would also be reasonable. Besides C—C bond cleavage that would lead to N-formyl products—as undergone by 1,2-dioxetanes in some structural systems and reaction conditions—peroxide intermediates may also undergo C—N bond cleavage to produce aldehydes plus (at least transient) free amines. (Ando, W.; Saiki, T.; Migita, T. J. Am. Chem. Soc. 1975, 97, 5028.) Often, including structure 3 in the present system (Scheme 2), such free amines may react with aldehyde (e.g., acetaldehyde) molecules generated from C—C bond cleavage at other enamine sites to form new enamines that are themselves susceptible to continued reaction with singlet oxygen.

Figure 6:
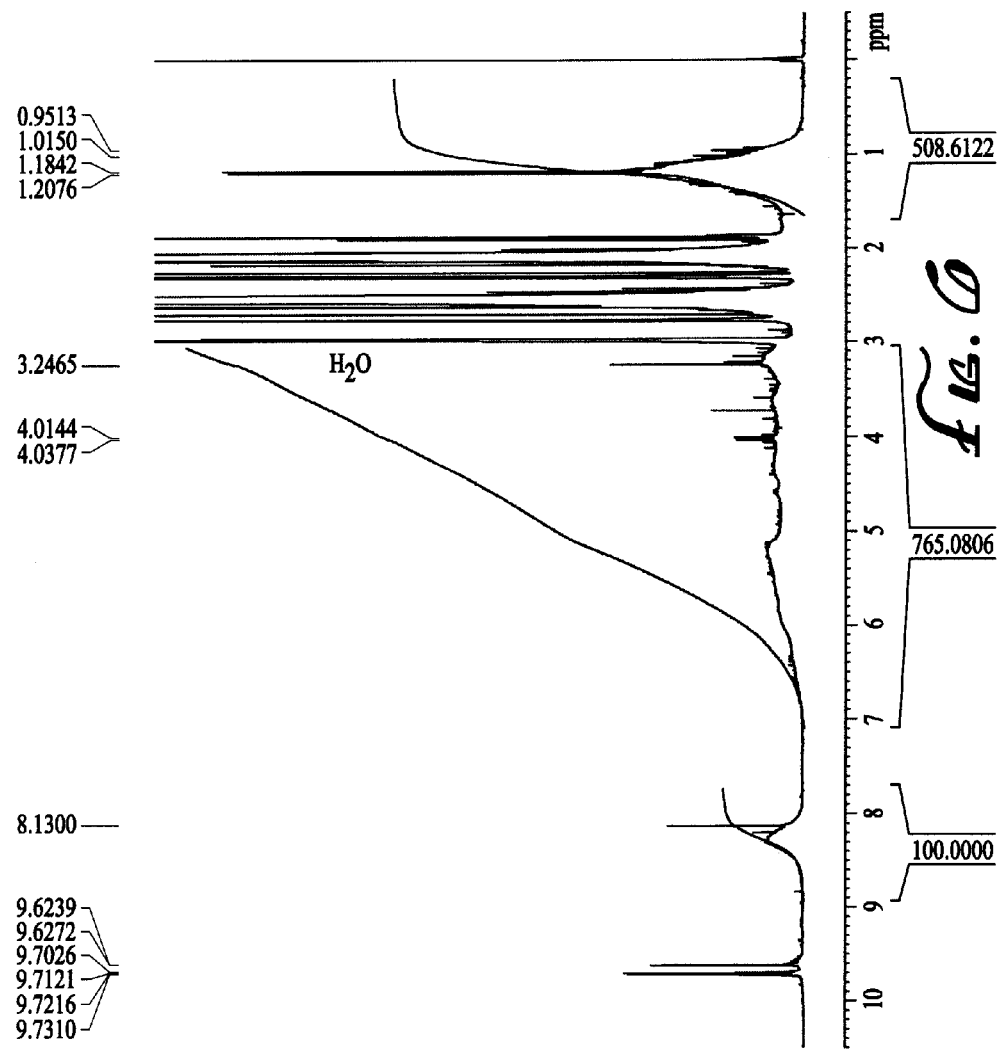
FIG. 6 is a chart of the $^1$H NMR absorption spectra of a reaction solution following photooxygenation of HPIW.

Further direct evidence of C—N bond cleavage as an alternative mode of peroxide intermediate degradation was seen in our experiments. Expected by-products of such cleavage from N-propenyl photooxygenation intermediates would be 2-hydroxypropionaldehyde (lactaldehyde) and methylglyoxal. (Ando et al.) Both of these compounds are fairly reactive species and tend to hydrate and/or dimerize in various ways. Lactaldehyde forms an equilibrium mixture of three different conformations of 3,6-dimethyl-1,4-dioxane-2,5-diol (structure 4). (Takahashi, H.; Kobayashi, Y.; Kaneko, N. Spectrochim. Acta 1983, 39A, 569.) Methylglyoxal may also form similar hydrated forms and/or cyclic dimers or trimers, such as 2,5-dimethyl-1,4-dioxane-2,3,5,6-tetraol (structure 5), depending on conditions. (Nemet, I.; Vikić-Topić, D.; Varga-Defterdarovićc, L. Bioorg. Chem. 2004, 32, 560.) It is revealing now that 1H NMR spectra of reaction solution aliquots from photooxygenations of HPIW (FIG. 6) show very complex absorptions in aliphatic proton regions that appear consistent with containing the complex patterns that are apparent in spectra of lactaldehyde dimer (FIG. 9) as well as methylglyoxal (FIG. 10).

Finally, one species that forms in HPIW photooxygenation reaction solutions under some conditions (FIG. 6) exhibits a relatively simple $_1$H NMR pattern [δ 1.196 (d, 7.0 Hz), 4.028 (q of d, 7.0 Hz, 0.97 Hz), 9.626 (d, 0.97 Hz)] that is qualitatively very similar to—but not identical to—known 2-hydroxypropionaldehyde monomer [δ 1.14 (d, 7.25 Hz), 4.01 (CH), 5.55 (OH, JH—OH=5.5 Hz), 9.80 (CHO, JH—CHO=1.0 Hz)]. (Zioudrou, C.; Stassinopoulou, C. I.; Loukas, S. Bioorg. Chem. 1980, 9, 163.) Since the reaction product species lacks vicinal HC$_2$—OH coupling, it may be assigned as a chemically similar peroxide derivative (dimer 6 in Scheme 2) that could reasonably result from degradation of tetroxocane intermediate structure 2. Another observation that is consistent with long-term degradation (via C—N bond cleavage to produce aldehyde by-products) of initially isolated peroxide intermediates is that the storage of solid oxidation products produced a noticeable odor (which involatile hexaazaisowurtzitanes would not have), and storage under vacuum over phosphorus pentoxide allowed apparent absorption of organic material by the phosphorus pentoxide, which darkened somewhat during desiccation of the oxidation products.

Elemental analysis of one crop obtained from workup of the product of one photooxygenation reaction is consistent with a composition containing several of the components referred to above. It is not consistent with a single specific hexaazaisowurtzitane derivative. It is believed, therefore, that the product material contains a mixture of hexaazaisowurtzitanes with various substituents as suggested in Scheme 2: initially isolable peroxide intermediates leading, on storage, to ultimate products that should contain N-unsubstituted (NH) sites, N-formyl sites, and C—N cleavage products such as methylglyoxal. Following such cleavage, smaller byproducts might be separable from hexaazaisowurtzitanes, though they may not interfere with subsequent nitrolysis reactions anyway.

The yield of HPIW via base-catalyzed isomerization of HAllylIW is somewhat dependent on workup conditions. Conversions of HAllylIW to HPIW by potassium t-butoxide in DMSO-tetrahydrofuran solutions appear to be essentially quantitative, by NMR analyses. Efficiency of separation of HPIW from by-products of this isomerization (especially potassium salts) appears to be more condition-dependent. One experiment in which the crude product solution was heated (40~60° C.) during rotary evaporation—in order to remove DMSO solvent prior to redissolution in benzene— gave a relatively low isolated yield of 70% HPIW. Additional treatment of the benzene extract solution with n-pentane showed some precipitation of material consistent with polymeric degradation product(s) of HPIW. The benzene-pentane solution contained purer HPIW, but its yield was lower presumably due to degradation at elevated temperature.

In a second preparation of HPIW, the reaction product solution was split into two portions for separate workups. One half was initially treated similarly to previous preparations: THF under house vacuum and then DMSO under high vacuum were pumped off at ambient temperature. HPIW was dissolved from the residue by 1:1 benzene-pentane; the suspension was filtered; and the filtrate was concentrated by rotary evaporation. The yield of HPIW by this treatment was 93%; some residual solvents (benzene, DMSO) were still present (not included in this yield) but would not interfere with subsequent photooxygenation reactions.

The other half of the reaction product solution was extracted with hexanes, which removed most of the HPIW from the DMSO solution and gave a 69% yield (in the presence of some residual DMSO). The hexane-unextractable portion of the solution was treated "conventionally": solvents were removed under high vacuum at ambient temperature; HPIW was then extracted with benzene-pentane. This treatment produced an additional 15% HPIW. (Total yield: 84%.) Thus, extraction by hexanes could alleviate most of the DMSO removal, which could be unwieldy in a larger-scale production process, though there is some loss in yield this way. An alternative workup using longer-term liquid-liquid extraction at low temperature, such as with pentane, might improve this efficiency.

With a better understanding of the structural nature of products formed in photooxygenation reactions (Scheme 2), it is now recognized that the oxidation reactions that lead to nitrolyzable intermediates appear to be essentially quantitative, according to NMR characterizations of these reactions, since there are no residual propenyl groups apparent. Although the compositions of such reaction products may be very complex—due to the parallel pathways available for degradation of initial intermediates formed during singlet oxygen reaction—the hexaazaisowurtzitane products formed from these pathways are nitrolyzable. However, nitrolysis of theoretically nitrolyzable precursors is not necessarily quantitative. Thus, nitrolytic cleavage of hemiaminal substituents (as in structure 2) may be more or less efficient than nitrolytic replacement of N-formyl groups, and both of these electrophilic substitutions should be less efficient—or least kinetically slower—than simple nitration of N-unsubstituted intermediates present from C—N bond cleavage of peroxide intermediates. Such N-unsubstituted intermediates may be indefinitely stable if proximate nitrogens are protected, as the structures would be chemically similar to tetraacetylhexaazaisowurtzitane (TADH), the preferred precursor in the current production process for CL-20.

Figure 7:
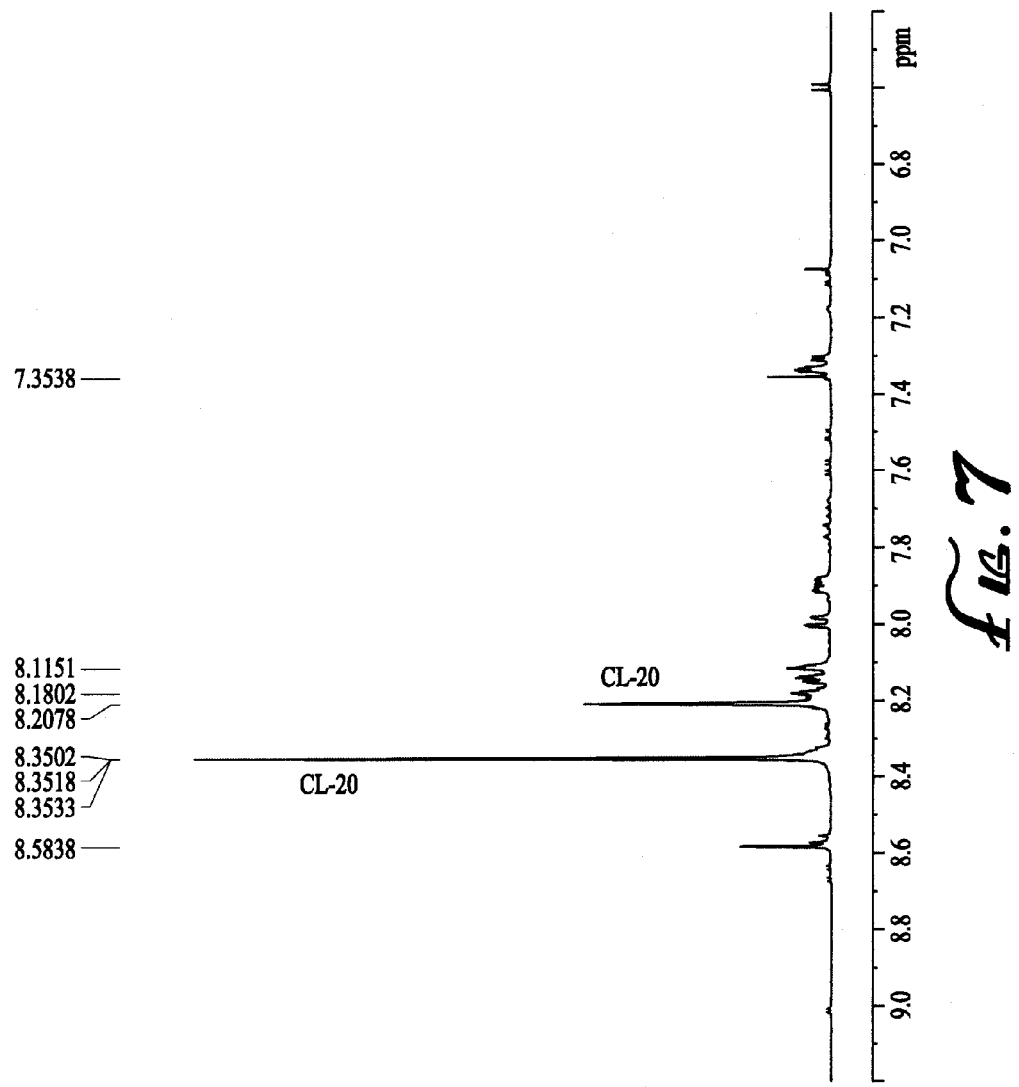
FIG. 7 is a chart of the $^1$H NMR absorption spectra in the hexaazaisowurtzitane (CL-20) cage proton region.
Figure 8:
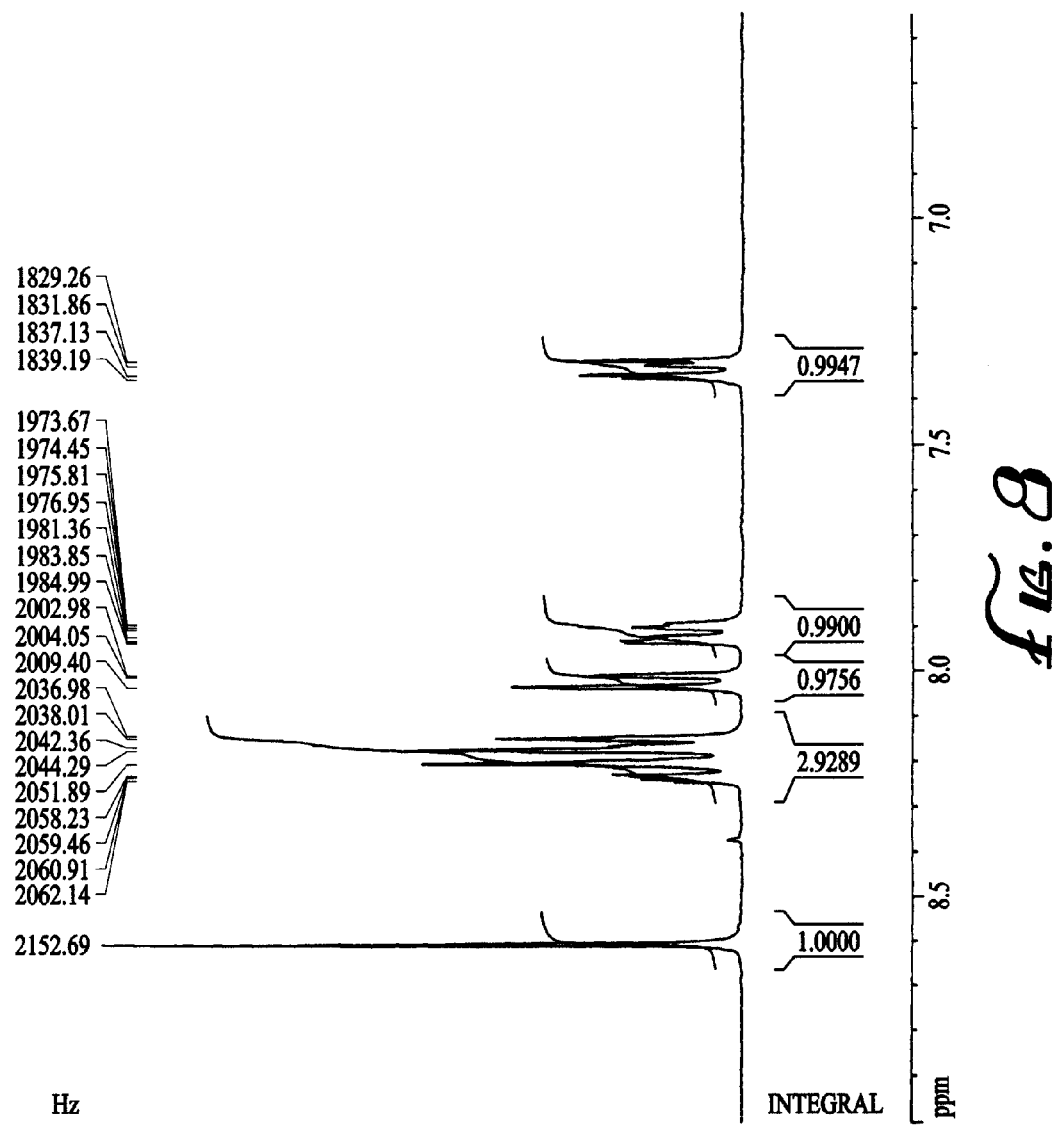
FIG. 8 is a chart of the $^1$H NMR absorption spectra of a mixture of predominantly 4-formylpentanitrohexaazaisowurtzitane and a lesser amount of 4,10-diformyltetranitrohexaazaisowurtzitane.

The relative nitrolyzability of the various substituents was investigated in one nitrolysis experiment conducted on a sample of photooxygenation product. One nitrolysis was performed using a solid sample of a product precipitated from photooxygenation in acetone solvent. A solution of the solid product dissolved in nitric acid, in the presence of Nafion® NR50 acid catalyst, was refluxed for 26½ hours. After neutralization and extraction with dichloromethane, the solute's hexaazaisowurtzitane composition appeared to be only ~52 mol % CL-20. The balance of absorptions in the hexaazaisowurtzitane cage proton region of the $_1$H NMR spectrum (FIG. 7) looked remarkably like a mixture of predominantly 4-formylpentanitrohexaazaisowurtzitane (WFN$_5$) and a lesser amount of 4,10-diformyltetranitrohexaazaisowurtzitane (sym-WF$_2$N$_4$), by comparison to their published spectral (WFN$_5$ in FIG. 8). This result is consistent with easier susceptibility to nitrolysis of the hexaazaisowurtzitane cages' imidazolidine nitrogens than of the piperazine ring nitrogens. This result has been similarly observed in past nitrolyses of tetraacetyldiformylhexaazaisowurtzitane (TADF).

Another nitrolysis experiment under similar conditions— with a different sample of photooxygenation product—was allowed to run for 44½ hours to ensure complete nitrolysis. This experiment utilized a workup of quenching into icewater, neutralization with solid sodium bicarbonate, and filtering off precipitated CL-20. A yield could be calculated for this nitrolysis even without knowing the exact composition of the photooxygenation product, since elemental analysis of the material is available and an assumption is made that all of the nitrogen in the reactant sample is present in the form of hexaazaisowurtzitane derivatives, since no nitrogen is introduced by any other treatment of the material. The observed yield for this run under these conditions was 47%. Conditions for nitrolysis of this intermediate were not optimized in any way. Optimal nitrolysis times may be dependent on the chemical composition of the intermediate mixture, and they may occur in between the times of 26½ hours and 44½ hours used in these two experiments. Alternative nitrolysis reagents and acid catalysts might prove to be superior following adequate process development as would be apparent to one or ordinary skill in the art.

An alternative pathway to CL-20 from HPIW which we have previously demonstrated is via its direct nitrolysis. A repetition of that experiment—using conditions similar to those for nitrolysis of the photooxygenation product, but with a reaction time of 94 hours to ensure complete nitrolysis— provided an isolated yield of CL-20 of only 11.6%. Again, reaction conditions were in no way optimized, and shorter nitrolysis times might provide higher yields. From these results, however, it appears worthwhile to carry out oxidation of HPIW to stable, nitrolyzable intermediates, which seem to survive nitrolysis conditions better (as intact hexaazaisowurtzitane cages) than HPIW itself. Further, a sample of HAllyIIW subjected to similar nitrolysis conditions for 46 h showed no or negligible evidence of the formation of CL-20, according to $^1$H NMR analysis.

Experimental Section

Hexaallylhexaazaisowurtzitane (HAllyIIW). To 10.6 g of allylamine dissolved in 30 mL of acetonitrile was added 1.2 g of formic acid (99%) plus 0.2 mL of water. After cooling to 0° C., 9.0 g of 40% aqueous glyoxal was added over 1 h with stirring. The solution was then stirred for an additional hour at 0° C.; then 24 mL of saturated sodium bicarbonate was added and stirring continued at 0° C. for one more hour. After standing in the freezer (−16° C.) overnight, the product was filtered, washed with water, and air dried for 2 h, giving 3.46 g of an off-white soft solid. The product was dissolved in 25 mL of dichloromethane, dried over $MgSO_4$, filtered, and evaporated to an off-white crystalline solid. This was pumped under high vacuum for 1 h, giving 3.32 g of product (26% yield). Sodium bicarbonate is mildly alkaline having a $pK_a$ of 6.3 in water. It will be apparent to one or ordinary skill in the art that other weak acids having similar $pK_a$ in water to formic acid may be utilized and are within the scope of the invention. It will likewise be apparent to one or ordinary skill in the art that other weak alkaline moieties having similar $pK_a$ in water to sodium bicarbonate may be utilized and are within the scope of the invention.

Figure 3:
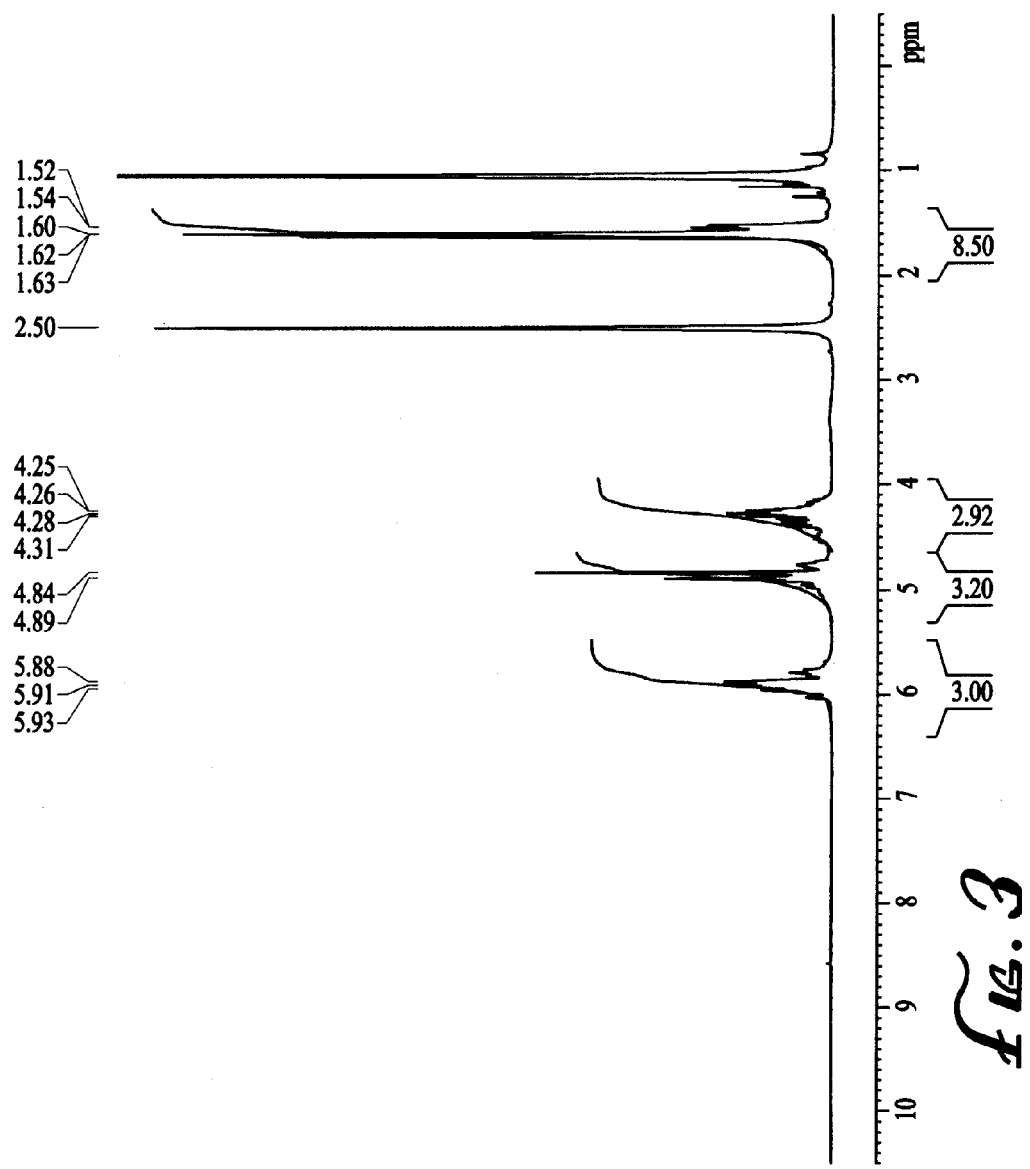
FIG. 3 is a chart of the $^1$H NMR (DMSO-$d_6$) spectrum of HPIW in a selected reaction mixture.
Figure 4:
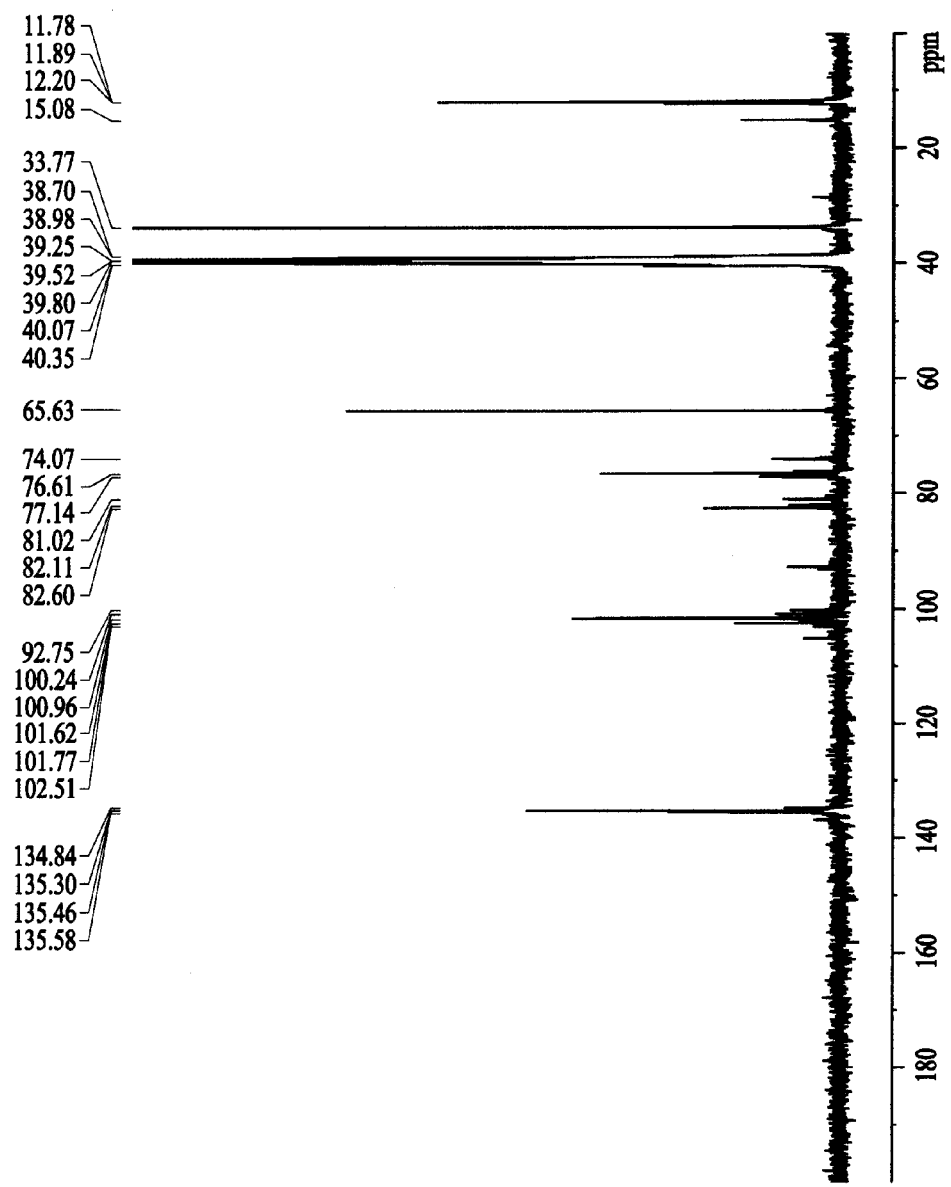
FIG. 4 is a chart of the $^{13}$C NMR (DMSO-$d_6$) spectrum of HPIW in the selected reaction mixture of FIG. 3.

Hexa(1-propenyl)hexaazaisowurtzitane (HPIW) (Procedure A). Hexaallylhexaazaisowurtzitane (HAllyIIW) was prepared following Nielsen as discussed above, and similarly to the procedure reported by Hervé et al. but with the significant modification that the product solution was basified with saturated aqueous $NaHCO_3$ and then stored at −16° C. thereby precipitating HAllyIIW. HAllyIIW (1.00 g) was dissolved in 4.0 mL anhydrous DMSO plus 1.0 mL DMSO-do plus 3.0 mL of a 20 wt % solution of potassium t-butoxide in tetrahydrofuran, and the mixture was magnetically stirred overnight at ambient temperature. After ~18 h, isomerization of HAllyIIW to HPIW was complete by NMR analysis. THF was removed at ambient temperature under vacuum, and the temperature was raised (40~60° C.) to remove DMSO Residual DMSO was pumped off at high vacuum and ambient temperature overnight. The residue was shaken with benzene (~25 mL), and the suspension was filtered. To the filtrate was added an equal volume of n-pentane, which precipitated a small amount of amber solid, which was filtered off. The filtrate was concentrated by rotary evaporation at ambient temperature. Pentane was added to the residue, and the suspension was filtered again. The solution was concentrated by rotary evaporation, and the residue was left under high vacuum for 3 days. Yield: 0.7035 g (70%). NMR analysis of the residue in acetone-$d_6$ showed it to be relatively quite pure HPIW. $^1$H NMR ($CD_2Cl_2$): δ 1.59-1.70 (m, $CH_3$), 4.42-4.76 (m, $CHCH_3$), 4.75 (s, 4H, cage CH), 4.84 (s, 2H, cage CH), 5.93-6.02 (NCH). $^{13}$C NMR ($CD_2Cl_2$): δ 12.46, 12.57, 12.82, 15.49, 75.67, 75.81, 77.95, 78.30, 78.71, 78.85, 78.94, 81.92, 82.48, 83.35, 83.89, 95.45, 102.85, 103.78, 104.38, 104.87, 105.90, 135.47, 135.59, 135.76, 135.88, 136.09. Progress of the isomerization was monitored occasionally by $^1$H NMR analysis of small aliquots. The $^1$H NMR (DMSO-$d_6$) spectrum of HPIW in the crude reaction mixture (FIG. 3): δ 1.52-1.63 (m, $CH_3$), 4.24-4.33 (m, $CHCH_3$), 4.84 (s, 4H, cage CH), 4.89 (s, 2H, cage CH), 5.88-5.96 (NCH). Similarly, the $^{13}$C NMR (DMSO-$d_6$) spectrum of the crude reaction mixture is shown in FIG. 4: δ 11.78, 11.89, 12.20, 15.08, 74.07, 76.61, 77.14, 81.02, 82.11, 82.60, 92.75, 100.24, 100.96, 101.62, 101.77, 102.51, 134.84, 135.30, 135.46, 135.58.

Hexa(1-propenyl)hexaazaisowurtzitane (HPIW) (Procedure B). To HAllyIIW (3.16 g, 7.75 mmol) dissolved in 15 mL anhydrous DMSO was added 7.0 mL (11.6 mmol) of a 20 wt % solution of potassium t-butoxide in tetrahydrofuran, and the mixture was magnetically stirred overnight at ambient temperature. The reaction solution was divided into two equal portions for separate workups. Workup 1: THF was removed at ambient temperature under vacuum, and DMSO was pumped off at high vacuum and ambient temperature overnight. The residue was shaken with ~100 mL of 1:1 benzene-pentane, and the suspension was filtered. The filtrate was concentrated by rotary evaporation at ambient temperature; pentane was added to the residue, and the suspension was filtered again. The solution was concentrated by rotary evaporation, and the residue was left under high vacuum for 4 days. The residue was dissolved in $CCl_4$ to a volume of 9.6 mL. NMR analysis of a sample showed it to contain some residual solvents in addition to usably pure HPIW. Contained yield of HPIW: $1.46_6$ g (93%).

Workup 2: The other half of the reaction solution was stirred vigorously overnight with 80 mL of hexanes. The hexanes layer was harvested or collected by decanting, and the DMSO layer was rinsed with 5-10 mL hexanes, which was added to the first hexanes solution. The collected hexanes solution was treated with a little $MgSO_4$, filtered, and evaporated to a pinkish oil. NMR analysis (DMSO-$d_6$) of a sample showed it to contain some residual DMSO in addition to quite pure HPIW. Contained yield of HPIW: $1.09_0$ g (69%). The DMSO layer was processed as in Workup 1 above. NMR analysis of a sample showed it to contain some residual solvents in addition to usably pure HPIW. Contained yield of HPIW: $0.24_4$ g (15%). Total yield of Workup 2: 84%.

Photooxygenation of HPIW (Procedure A). The HPIW product from Procedure A above was dissolved in 10 mL of acetone-$d_6$ in a 10-mL graduated cylinder (with a standard-taper joint) fitted with a Claisen adapter to allow inlet as well as egress of an oxygen purge via a glass capillary; a few mg of zinc(II) tetraphenylporphine sensitizer was added to the solution, and the base of the cylinder was submerged in a dry ice-ethanol bath [~−78° C.]. With a purge of oxygen passing through, the solution was irradiated with a quartz halogen headlamp. After 4 h of treatment, a pale pink flocculent solid was suspended in the solution. The suspension was filtered, and the filtrate was subjected to additional reaction with singlet oxygen for a couple of hours. A small amount of additional solid precipitated, which was filtered off. The filtrate in acetone-$d_6$ was reduced in volume by rotary evaporation. An equal volume of chloroform was then added, which precipitated more pale pink solid, which was filtered off. All filtered solids were dried in a vacuum desiccator over $P_4O_{10}$. Melting-point determination of the first precipitate from the reaction showed it to darken starting at 149° C., melting with decomposition above 180° C. with evolution of a clear condensable liquid. Elemental analysis was determined for the final precipitate from chloroform (%, mean of two): C, $47.64_5$; H, 5.61; N, $18.97_5$; O (by difference), 27.77. A qualitative peroxide test was conducted on some of the final precipitate from chloroform: 9.0 mg in ~½ mL DMSO-$d_6$ was added to a solution of ~½ g KI plus 1 mL acetic acid in ~10 mL water, producing a yellowish color; addition of starch solution produced a distinct blue color in <1 min. A control test with all components (including DMSO) except the oxidation product showed no color change.

The final precipitate's main broad $_1$H NMR absorptions—formyl CHO, oxygenated substituent $CH_3$, and other aliphatic protons including cage CH—proposed for the product mixture (Scheme 2) show relative integrations consistent with a formulation of $(C_6H_6N_6)(CHO)_{3.428}(C_6H_{10}O_4)_{1.286}$ where $C_6H_{10}O_4$ may be due to residual tetroxocane intermediate (occupying two cage nitrogens as in 2) or two dissociated propionaldehyde derivatives, such as methylglyoxal, leaving residual unsubstituted free (NH) nitrogens.

Photooxygenation of HPIW (Procedure B). The HPIW product from Procedure B (hexanes extract of Workup 2) above was dissolved in 25 mL of 1:1 DMSO-acetone in a 25-mL graduated cylinder (with a standard-taper joint) fitted with a Claisen adapter to allow inlet as well as egress of an oxygen purge via a glass capillary; a few mg of zinc(II) tetraphenylporphine sensitizer was added to the solution, and the base of the cylinder was submerged in a dry ice-ethanol bath. With a purge of oxygen passing through, the solution was irradiated with a quartz halogen headlamp. After 5.6 h of treatment, the solution remained homogeneous, but NMR analysis of an aliquot (FIG. 6) showed no residual propenyl signals, so their oxidation was complete. A positive qualitative peroxide test, as in Procedure A, was obtained from the solution. Attempts to identify components of the product by electrospray ionization mass spectroscopy as well as by atmospheric pressure chemical ionization (APCI) mass spectrometry under a variety of conditions were not conclusive.

Partial nitrolysis of oxidation product to CL-20. Some of the first precipitate (203 mg) from photooxygenation Procedure A (previously vacuum-dried over $P_4O_{10}$) was wetted with ~1 mL $CCl_4$ in a 50-mL round-bottom flask—containing a stirbar and fitted with an addition funnel containing 15 mL of cold 98~100% nitric acid (Fluka "100%" nitric acid) and a nitrogen bubbler—and cooled in a dry ice—dichloromethane bath [~−78° C.]. The nitric acid was added quickly via the addition funnel. When the nitric acid started freezing, the cooling bath was removed, and the organic reactant dissolved in the acid upon warming adventitiously. After the solution reached room temperature, Nafion® NR50 beads (0.77 g) were added, and the solution was heated to reflux—with a nitrogen bubbler atop the reflux condenser—in an oil bath maintained at 88±5° C. After 26½ h reflux, 8.7 mL of the reaction was quenched onto a mixture of ice plus aqueous $NaHCO_3$ to neutralize the solution. The aqueous solution/suspension was extracted with $CH_2Cl_2$ (4×60 mL), which was removed by rotary evaporation. NMR analysis of the residue (FIG. 4) showed ~52% conversion to CL-20, the balance being mostly $WFN_5$.

Nitrolysis of oxidation product to CL-20. Some of the final chloroform precipitate (123.3 mg previously vacuum-dried over $P_4O_{10}$) from photooxygenation Procedure A in a 25-mL round-bottom flask—containing a stirbar and fitted with an addition funnel containing 15 mL of cold 98~100% nitric acid (Fluka "100%" nitric acid) and a nitrogen bubbler—was cooled in a dry ice-dichloromethane bath. The nitric acid was added quickly via the addition funnel. When the nitric acid started freezing, the cooling bath was removed, and the organic reactant dissolved in the acid upon warming adventitiously. After the solution reached room temperature, Nafion® NR50 beads (0.77 g) were added, and the solution was heated to reflux—with a nitrogen bubbler atop the reflux condenser—in an oil bath maintained at 92±4° C. NMR analysis of an aliquot in $CD_3CN$ showed nitrolysis to be incomplete after 29 h, so reflux was continued. After 44½ h reflux, the reaction was quenched onto ice and solid $NaHCO_3$ was added to neutralize the solution (~60 mL). White solid CL-20 was filtered off and vacuum-dried over $P_4O_{10}$. Yield: 57.5 mg (47% based on nitrogen analysis of the reactant).

Figure 5:
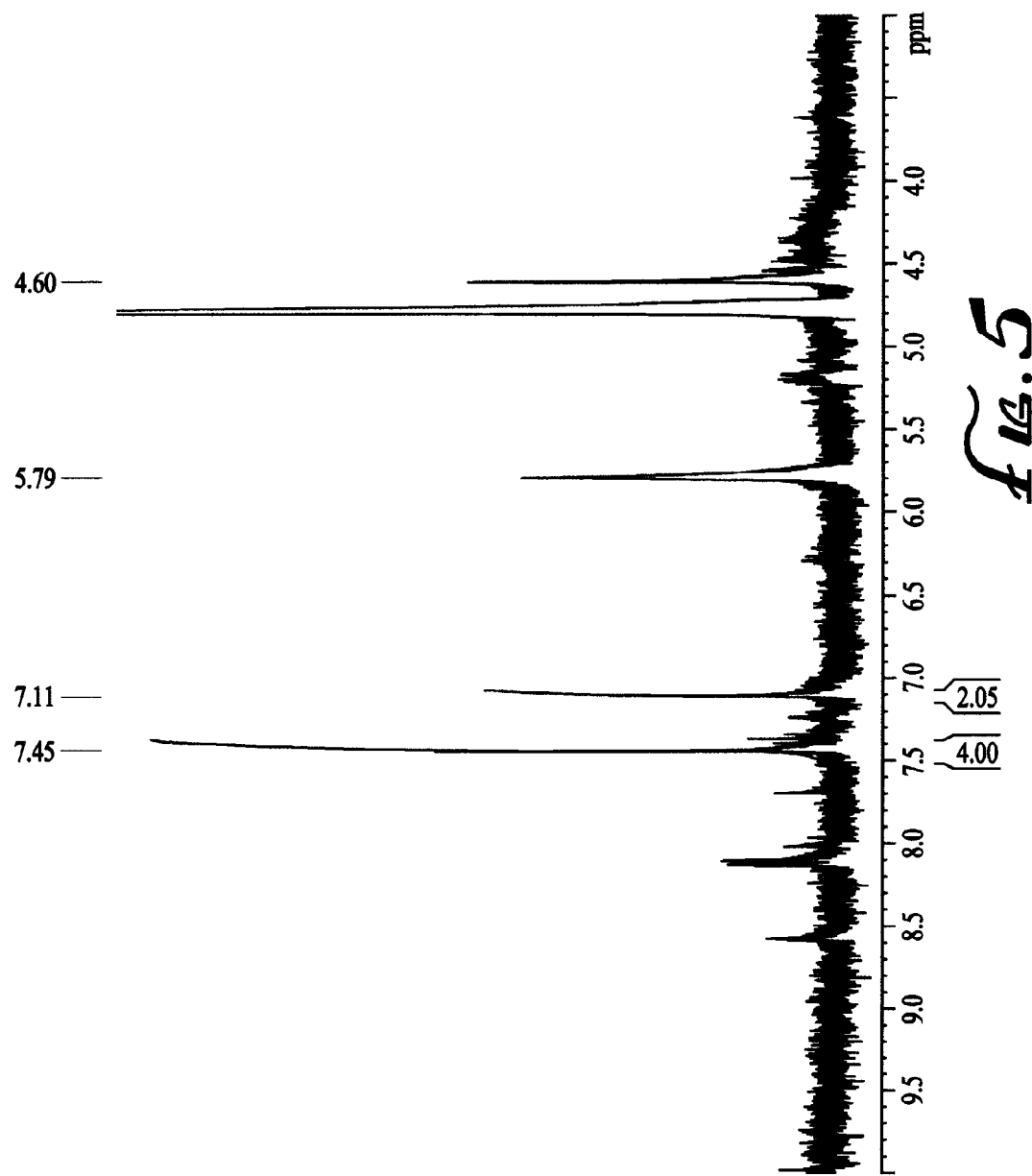
FIG. 5 is a chart of the $^1$H NMR absorption spectral region attributable to hexaazaisowurtzitane following nitrolysis of HPIW to hexaazaisowurtzitane.

Nitrolysis of HPIW to CL-20. A solution (1.0 mL) containing 170. mg HPIW in $CCl_4$ (Procedure B, Workup 1) in a 50-mL round-bottom flask—containing a stirbar and fitted with an addition funnel containing 15 mL of cold 98~100% nitric acid (Fluka "100%" nitric acid) and a nitrogen bubbler—was cooled in a dry ice-dichloromethane bath. The nitric acid was added quickly via the addition funnel. When the nitric acid started freezing, the cooling bath was removed, and the organic reactant dissolved in the acid upon warming adventitiously. After the solution reached room temperature, Nafion® NR50 beads (0.77 g) were added, and the solution was heated to reflux—with a nitrogen bubbler atop the reflux condenser—in an oil bath maintained at 92±4° C. NMR analysis of an aliquot in $CD_3CN$ showed nitrolysis to be incomplete after 29 h, so reflux was continued. After 94 h reflux, the reaction was quenched onto ice and solid $NaHCO_3$ was added to neutralize the solution. White solid CL-20 was filtered off and vacuum-dried over $P_4O_{10}$. Yield: 17.5 mg (11.6%). A sample withdrawn into dichloromethane-$d_2$ showed, by $^1H$ NMR (FIG. 5), significant simplification of the hexaazaisowurtzitane region and formation of CL-20, confirmed by addition of a small amount of authentic CL-20 to the NMR sample and observation of the increase of specific peaks. $^1H$ NMR ($CD_2Cl_2$ with $HNO_3$, vs. trimethylsilylpropionic-$d_4$ acid as δ 0.00) of contained CL-20: δ 7.11 (2H), 7.45 (s, 4H).

While the present invention has been described in connection with what are currently considered to be the most practical and preferred embodiments, it is to be understood that the invention is not to be limited to the disclosed embodiments, but to the contrary, is intended to cover various modifications, embodiments, and equivalent processes included within the spirit of the invention as may be suggested by the teachings herein, which are set forth in the appended claims, and which scope is to be accorded the broadest interpretation so as to encompass all such modifications, embodiments, and equivalent processes.

What is claimed is:

1. A process for preparing hexaallylhexaazaisowurtzitane (HAllylIW) comprising:
   dissolving allylamine in a mixture of polar organic solvent and water to form a first composition;
   acidifying said first composition with a Bronsted acid in water to form an acidic second composition;
   cooling said second composition to about 0° C.;
   mixing said second composition, at about 0° C., with an aqueous solution of glyoxal to form a third composition;
   stirring said third composition at about 0° C. until acid catalysis of reaction between allylamine and glyoxal is substantially complete to form a fourth composition containing hexaallylhexaazaisowurtzitane in solution;
   basifying said fourth composition at about 0° C. with a Bronsted base in water to form a mildly basic fifth composition;
   stirring said fifth composition, allowing contact of reactants, at about 0° C. for a predetermined period of time to form a sixth composition;
   chilling said sixth composition to about minus 16° C. or lower allowing precipitation of hexaallylhexaazaisowurtzitane to form a seventh composition; and
   separating said precipitated hexaallylhexaazaisowurtzitane from said seventh composition.

2. The process for preparing hexaallylhexaazaisowurtzitane of claim 1 wherein:
   said Bronsted acid has a pKa in water less than about 5.

3. The process for preparing hexaallylhexaazaisowurtzitane of claim 1 wherein:
   said Bronsted acid is formic acid.

4. The process for preparing hexaallylhexaazaisowurtzitane of claim 1 wherein:
   said Brönsted base has a pKa in water greater than about 5.

5. The process for preparing hexaallylhexaazaisowurtzitane of claim 1 wherein:
   said Bronsted base has a pKa in water of about 6.3.

6. The process for preparing hexaallylhexaazaisowurtzitane of claim 1 wherein:
   said Bronsted base is an aqueous solution of sodium bicarbonate.

7. The process for preparing hexaallylhexaazaisowurtzitane of claim 1 wherein:
   said Bronsted base is a saturated aqueous solution of sodium bicarbonate.

8. The process for preparing hexaallylhexaazaisowurtzitane of claim 1 wherein:
   said aqueous solution of glyoxal is about a 40% solution.

9. The process for preparing hexaallylhexaazaisowurtzitane of claim 1 wherein:
   said polar organic solvent is acetonitrile.

\* \* \* \* \*